United States Patent [19]

Hay

[11] 4,374,974

[45] Feb. 22, 1983

[54] METHOD FOR MAKING POLYFORMALS AND POLYFORMAL PRODUCTS MADE THEREBY

[75] Inventor: Allan S. Hay, Schenectady, N.Y.

[73] Assignee: General Electric Company, Schenectady, N.Y.

[21] Appl. No.: 958,040

[22] Filed: Nov. 6, 1978

Related U.S. Application Data

[63] Continuation of Ser. No. 889,393, Mar. 23, 1978, abandoned.

[51] Int. Cl.³ ............................................. C08G 65/40
[52] U.S. Cl. .................................... 528/219; 528/126; 528/128; 528/174; 528/205; 549/347; 549/352; 549/353
[58] Field of Search ............... 528/219, 126, 128, 174, 528/205; 549/347, 352, 353

[56] References Cited

U.S. PATENT DOCUMENTS 3,069,386 12/1962 Barclay, Jr. .................... 528/219

Primary Examiner—Lester L. Lee
Attorney, Agent, or Firm—William A. Teoli; James C. Davis, Jr.

[57] ABSTRACT

There are provided linear aromatic polyformal compositions and cyclic polyformals. A method is also provided for making linear aromatic polyformals having reduced aromatic cyclic polyformal content to provide transparent films having improved Notched Izod Impact. The cyclic aromatic polyformals can be used as intermediates for making solvent resistant organic wire coating formulations.

22 Claims, No Drawings

METHOD FOR MAKING POLYFORMALS AND POLYFORMAL PRODUCTS MADE THEREBY

This is a continuation of application Ser. No. 889,393, filed Mar. 23, 1978, now abandoned.

The present invention relates to film forming aromatic polyformal resins, cyclopolyformals and method for making such materials.

As shown in my copending application Ser. No. 739,562, film forming aromatic polyformals consisting essentially of chemically combined units of the formula, $$-OROCH_2-, \qquad (1)$$

where R is a divalent aromatic organic radical defined more particularly below, can be made by directly agitating a mixture of methylene halide, bisphenol, alkali metal hydroxide with either a phase transfer catalyst, or a dipolar aprotic solvent. Another procedure which can be used to make low molecular weight aromatic polyformal resin is shown by Barclay U.S. Pat. No. 3,069,386. The method of Barclay requires the production of a diphenolate preform prior to its condensation with methylene halide.

It has been found that although the procedure of Ser. No. 739,562 can be used to make film forming aromatic polyformals, the resulting compositions can contain up to about 50% by weight of cyclopolyformals of the formula, $$\left[-OROCH_2-\right]_n \qquad (2)$$

where R is the same as in formula (1), and n is an integer equal to from 2 to 25 inclusive.

Radicals included by R of formulas 1 and 2 are $C_{(6-25)}$ divalent aromatic radicals, for example, phenylene, tolylene, xylylene, naphthalene, etc.; halogenated derivatives of such divalent aromatic hydrocarbon radicals, such as chlorophenylene, bromotolylene, etc., divalent radicals, such as $-R^1QR^1-$, where $R^1$ is selected from $C_{(6-13)}$ divalent aromatic radicals, Q can be cyclohexyl, fluorenyl, $-O-$, $-S-$, $$-\overset{O}{\underset{\|}{C}}-, \quad -\overset{O}{\underset{\|}{\underset{O}{S}}}-,$$

and $-C_yH_{2y}-$ and y is equal to 1 to 5 inclusive.

The film forming aromatic polyformals of the present invention consisting essentially of chemically combined units of formula (1) having an intrinsic viscosity of greater than 0.3 in chloroform at 25° C. and capable of being compression molded to a flexible film can be made by a method which comprises (A) agitating a mixture containing as essential ingredients, a bisphenol of the formula, $$HO-R^2-OH, \qquad (3)$$

methylene halide, alkali metal hydroxide and a member selected from a phase transfer catalyst or a dipolar aprotic solvent where there is utilized in the reaction mixture, per mole of bisphenol, more than 1 mole of methylene halide and greater than 2 moles of alkali metal hydroxide, where $R^2$ includes R radicals defined above, and $R^1Q'R^1$ radicals, where Q' is selected from Q radicals, $$-\overset{\|}{\underset{\overset{C}{\diagup}\diagdown}{C}}-, \text{ and } -\overset{}{\underset{C-Cl_3}{CH}}-, \text{ and}$$
$$Cl \quad Cl$$

(B) recovering aromatic polyformal from the mixture of (A).

In particular instances, where the dipolar aprotic solvent is used in the aromatic polyformal mixture, linear aromatic polyformal can be made having less than 10% by weight of cyclopolyformal of formula (2). Some low cyclic aromatic polyformals have been found to have improved clarity and Notched Izod Impact values. The compression moldable flexible film forming aromatic polyformals of the present invention having an intrinsic viscosity of greater than 0.3 dl/g in chloroform at 25° C. and consisting essentially of chemically combined units of formula (1), and having less than 10% by weight of such chemically combined units in the cyclic state can preferably be made by the method which comprises, (C) effecting reaction between a bisphenol of formula (3), and an alkali metal hydroxide in the presence of a mixture of methylene halide and a dipolar organic solvent, and (D) recovering aromatic polyformal from the reaction mixture of (C), where there is utilized in the reaction mixture of (C), from 2 to 2.5 moles of alkali hydroxide, per mole of bisphenol, a concentration of from 20 to 50% by weight of solids and a weight ratio of 0.8 to 1.2 part of dipolar aprotic solvent, per part of methylene halide.

An additional method for making aromatic polyformal having a low cyclic content is shown in copending application Ser. No. 889,397, now U.S. Pat. No. 4,260,733, filed concurrently herewith of Loucks and Williams, and assigned to the same assignee as the present invention. In accordance with the Loucks et al method, an antisolvent such as a methanol-acetone solution containing a minor amount of acetic acid is added to an agitated polyformal solution in accordance with a reverse precipitation technique to produce a substantially cyclic-free aromatic polyformal.

Some of the aromatic polyformals of the present invention, for example, those derived from bisphenol-A, can have tensile strengths of about 7,000 psi with 110% elongation, and Gardner impact values greater than 320 in/lbs. The polyformals of the present invention also have been found to possess a low degree of permeability to moisture. When converted to copolymers by standard phosgenation techniques or blended with various thermoplastic materials, it is found that they impart improved properties thereto.

Included in the bisphenols of formula (3) which can be used in the practice of the present invention to make the aromatic polyformals, are, for example,
2,2-bis(4-hydroxyphenyl)propane (Bisphenol-A);
2,4'-dihydroxydiphenylmethane;
bis-(4-hydroxyphenyl)methane;
1,1-bis-(4-hydroxyphenyl)ethane;
1,1-bis-(4-hydroxyphenyl)propane;
2,2-bis-(4-hydroxyphenyl)pentane;
3,3-bis-(4-hydroxyphenyl)pentane;

4,4'-dihydroxybiphenyl;
4,4'-dihydroxy-3,3',5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenyl sulfide;
hydroquinone;
resorcinol;
9,9'-bis(4-hydroxyphenyl)-fluorene;
3,4'-dihydroxydiphenylmethane;
4,4'-dihydroxybenzophenone;
4,4'-dihydroxydiphenylether;
2,2'-(4-hydroxyphenyl)-1,1-dichloroethylene;
2,2-bis(4-hydroxy-3-methylphenyl)propane;
2,2-bis(4-hydroxy-3,5-dimethylphenyl)propane;
1,1-bis(4-hydroxyphenyl)cyclohexane;
1,1-bis(4-hydroxy-3,5-dimethylphenyl)cyclohexane;
1,1-bis(4-hydroxy-3-methylphenyl)cyclohexane;
bis(4-hydroxy-3,5-dimethylphenyl)sulfone;
5-chloro-2,4'-dihydroxydiphenylsulfone;
4,4'-dihydroxydiphenyl ether;
4,4'-dihydroxy-2,5'-dimethyldiphenyl ether, etc.

Methylene halides which can be used in the practice of the invention are, for example, methylene chloride, methylene bromide, chlorobromomethane, etc. Alkali metal hydroxides which can be employed in the practice of the invention are, for example, potassium hydroxide which can be in the form of pellets, powder, etc., sodium hydroxide, etc.

The aromatic polyformals of the present invention also can be phosgenated to produce polyformal-polycarbonate copolymers. The polyformals of formula (1) and the polyformal-polycarbonate copolymers can be further blended with other thermoplastic organic resins, such as Lexan ® resin, PPO ® resin, Valox ® resin, all products of the General Electric Company, over wide proportions by weight, such as from 1% to 99% of the polyformal resin to 99% to 1% of the high performance thermoplastic organic resin. The polyformal resins of the present invention also can be blended with various fillers, such as glass fiber, silicon carbide whiskers, silica fillers, etc., stabilizers, pigments, flame retardants, etc.

In the practice of the invention, the aromatic polyformal can be made by effecting contact at a temperature of 0° C. to 100° C. and preferably 40° C. to 100° C., between methylene halide and bisphenol in the presence of alkali metal hydroxide. Reaction can be conducted between excess methylene halide and bisphenol until the latter has been completely reacted.

Reflux temperatures at atmospheric pressure or above atmospheric pressure can be used along with agitation of the mixture. Reaction between methylene halide and bisphenol in the presence of excess alkali metal hydroxide can be accelerated by using a substantially inert organic solvent in combination with methylene halide, such as a nonpolar or dipolar aprotic organic solvent. Nonpolar organic solvents which can be employed in the methylene halide are, for example, chlorobenzene, dichlorobenzene, benzene, toluene, etc. In addition, there can be used dipolar aprotic solvents, such as N-methylpyrrolidone, tetrahydrofuran, dimethylsulfoxide, etc.

Experience has shown that when methylene halide is employed in the absence of a dipolar aprotic solvent, effective results are achieved if a phase transfer catalyst is used to facilitate in situ formation of the alkali salt of the bisphenol and the subsequent condensation reaction with the methylene halide. Suitable phase transfer catalysts are, for example, quaternary ammonium and phosphonium salts, such as described in JACS 93, 195 (1971) by C. M. Starks. A proportion of from about 0.01 to 0.5 moles of the phase transfer catalyst per mole of the bisphenol has been found to provide for effective results, and preferably from 0.02 to 0.10 moles of phase transfer catalyst per mole of bisphenol can be employed.

The intercondensation reaction can be conducted over a period of from 0.1 hours to 24 hours or greater depending upon such factors as the nature of the methylene halide, whether an organic solvent is employed in combination with the methylene halide, the type of such organic solvent, temperature of the reaction, the degree of agitation, etc. In particular instances, for example, the more highly reactive methylene bromide can be substituted for methylene chloride or a mixture of chlorobenzene with methylene chloride will reflux at a higher temperature. In addition, the reaction can be conducted at elevated pressures, or in a closed system to permit the methylene halide to react with the bisphenol at a higher temperature. Those skilled in the art would know, for example, that the methylene halide itself, when used in excess amounts, can serve as a suitable organic solvent as well as a reactant.

The following examples are given by way of illustration and not by way of limitation. All parts are by weight, unless otherwise specified.

EXAMPLE 1

A mixture of 114 parts (0.5 mole) of bisphenol-A, 95 parts (1.7 mole) KOH pellets, 23.3 parts, (0.05 mole) of Aliquat 336 (95% active monomethyltricaprylyl ammonium chloride), a phase transfer catalyst of the General Mills Company, and 1,009 parts of methylene chloride was refluxed and stirred for a period of 21 hours under a nitrogen atmosphere. Water was then added to the mixture and the organic phase was separated and washed with water. A 70% yield of polymer was obtained by adding the organic layer to methanol and filtering and drying the resulting precipitate at 60° C. The polymer was found to have a $T_g$ of 85° C. and an intrinsic viscosity of 0.60 dl/g in chloroform at 25° C. The precipitate was then analyzed with a gel permeation chromatograph and found to contain aromatic cyclopolyformal. More specifically, the precipitate was found to consist of about 8.7% by weight of cyclic polyformal and the balance of the product was a linear polyformal consisting essentially of chemically combined units of the formula,

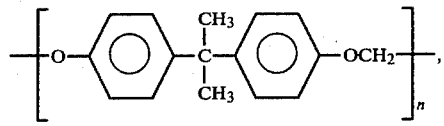

where n has an average value of 65.

The polymer was compression molded at 160° C. to produce a tough colorless flexible transparent film. A portion of the precipitated polymer was further analyzed with a high pressure liquid chromatograph. There was recovered a cyclic dimer having a melting point of 279° C. which had the following formula,

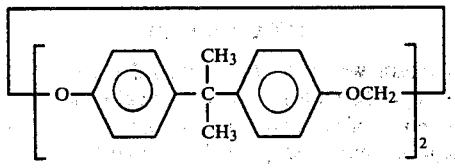

There was added a diethylether-BF₃ complex to a concentrated methylene chloride solution of the above polyformal dimer to produce a 1% by weight complex solution. The mixture was stirred with a metal spatula. A solvent resistant coating was found on the metal spatula after it was removed from the mixture and allowed to air dry. A cross-linking of the dimer had occurred which was confirmed by NMR.

A cyclic trimer was also recovered using HPLC having the following formula,

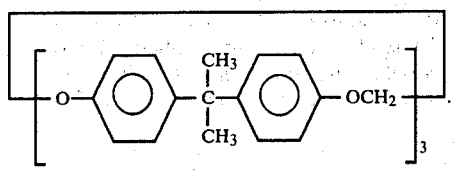

The trimer had a MP of 200° C.-250° C. The cyclic trimer and higher cyclics, where n in formula (2) is as high as 20, are also found to be useful to make metal coating compositions when used with a Lewis acid catalyst such FeCl₃, H₂SO₄, etc.

Typical physical properties of the above linear polyformal made by the above procedure are as follows:

| | |
|---|---|
| Tensile strength, p.s.i. at yield | 7-8000 |
| Tensile strength, p.s.i. at break | 7100-7500 |
| Elongation % | 110 |
| Density g/cm³ | 1.10 |
| Flexural strength p.s.i. | 14,300 |
| Flexural modulus 10⁵ p.s.k. 73° F. | 4.0 |
| Gardner impact strength | 320 in. lb. |

EXAMPLE 2

A mixture of dimethylsulfoxide, methylene chloride, potassium hydroxide, bisphenol-A, and Aliquat was stirred at a temperature of 60° C. for 4 hours under substantially anhydrous conditions. The mixture had a weight percent solids of 22% and a ratio of about 110 parts of dimethylsulfoxide per 90 parts of methylene chloride. In addition, there was utilized in the mixture, a ratio of 2.6 moles of potassium hydroxide per mole of the Bisphenol-A, while the Aliquat was employed in a proportion of about 0.1 mole of Aliquat per mole of the Bisphenol-A. There was obtained a polyformal having an intrinsic viscosity of 0.548 dl/g in chloroform at 25° C. Based on method of preparation, the polymer consisted essentially of chemically combined Bisphenol-A units and formaldehyde units. High pressure liquid chromatography and gel permeation chromatography indicated that the polymer had about 5.1% cyclics within the scope of the formula (2). A tough flexible film was obtained by compression molding, following the procedure of Example 1, or by casting from a chloroform solution.

EXAMPLE 3

A mixture of chlorobenzene, methylene chloride, potassium hydroxide pellets, bisphenol-A, tetrabutylammonium bromide and 1.9% by weight of water was stirred at 75° C. for a period of about 50 minutes. The mixture had a 19% solids content by weight, where the chlorobenzene was utilized in a proportion of about 9 parts of chlorobenzene per part of methylene chloride, while there was employed about 2.6 moles of potassium hydroxide per mole of bisphenol-A. In addition, the tetrabutylammonium bromide was present in the mixture in a proportion of about 0.1 mole of the phase transfer catalyst per mole of bisphenol-A.

There was obtained a 36% yield of polyformal from the above mixture having an intrinsic viscosity of 0.519 dl/g in chloroform at 25° C. and consisting essentially of chemically combined bisphenol-A units and formaldehyde units. High pressure liquid chromatography and gel permeation chromatography indicated that the polymer contained 27.6% by weight of cyclics within the scope of formula (2).

EXAMPLE 4

A mixture of 140.5 parts of N-methylpyrrolidone, 120.6 parts of methylene chloride, 21.8 parts of potassium hydroxide pellets and 34.25 parts of bisphenol-A was stirred for 39 minutes at 70° C. under substantially anhydrous conditions based on the aforementioned proportions. The polymerization mixture had about 17.7% solids based on the weight of the mixture and a ratio of about 2.6 moles of potassium hydroxide per mole of bisphenol-A. A polyformal was obtained consisting of chemically combined bisphenol-A units and formaldehyde units having an intrinsic viscosity of about 0.50 dl/g. High pressure liquid chromatography and gel permeation chromatography indicated that the polymer had 26.4% by weight cyclics. A tough flexible film was obtained from the polyformal following the above described casting or compression molding techniques.

EXAMPLE 5

The procedure of Example 4 was repeated, except that in place of the potassium hydroxide there was utilized 2.1 mole of sodium hydroxide per mole of bisphenol-A. There was also utilized about 1.16 part of N-methylpyrrolidone per part of methylene chloride, where the amount of solvent utilized provided for a mixture having about 24.3% by weight of solids, based on the weight of the mixture. After approximately one hour, there was recovered a 66% yield of a polyformal having an intrinsic viscosity of 0.80 dl/g. The polyformal was found to have about 5.2% by weight of cyclic based on high pressure liquid chromatography.

EXAMPLE 6

The procedure of Example 4 was repeated, except that there was utilized 1% by weight of p-t-butylphenol based on the weight of bisphenol-A. In addition, there was utilized sufficient bisphenol-A and potassium hydroxide to provide for about 18% by weight solids based on the weight of the mixture. No Aliquat phase transfer catalyst was used. There was obtained a polyformal having an intrinsic viscosity of 0.352 in chloroform at 25° C. and consisting essentially of chemically combined bisphenol-A units and formaldehyde units and chain stopped with p-tert-butylphenol units. The resulting polyformal having about 27.2% by weight cyclics of formula (2) was cast or compression molded to a tough flexible film.

The above procedure was repeated, except that 2% by weight of the chain stopper was used in the intercondensation mixture. It was found that the intrinsic viscosity of the polyformal had been reduced to 0.273. A further interconsendation reaction was attempted, free of chain-stopper using stoichiometric amounts of potassium hydroxide and bisphenol-A. It was found that even though the mixture had been heated and stirred for two hours at 70° C., the intrinsic viscosity of the resulting polyformal was 0.227. The low intrinsic viscosity of the polyformal indicated that more than a stoichiometric amount of potassium hydroxide was needed to produce polyformal having an intrinsic viscosity of at least 0.3 dl/g.

EXAMPLE 7

A mixture of methylene bromide, potassium hydroxide pellets, bisphenol-A and Aliquat phase transfer catalyst was heated for 10 minutes at 96° C. under substantially anhydrous conditions while the mixture was stirred. The mixture contained 11% by weight of solids and the potassium hydroxide was utilized in proportion of 4 moles of potassium hydroxide per mole of bisphenol-A while the phase transfer catalyst was employed in a proportion of 0.1 mole of catalyst per mole of bisphenol-A. There was obtained a polyformal consisting essentially of chemically combined bisphenol-A units and formaldehyde units having an intrinsic viscosity in chloroform of 1.9 at 25° C. The polyformal was cast or compression molded to a tough flexible film.

EXAMPLE 8

A mixture of methylene chloride, N-methylpyrrolidone, potassium hydroxide pellets and 9,9-bis(4-hydroxyphenyl)fluorene, "BPF", was stirred for 66 minutes at 70° C. under substantially anhydrous conditions. There was obtained a polyformal having an intrinsic viscosity of 0.638 and consisting essentially of chemically combined formaldehyde units and units of the formula,

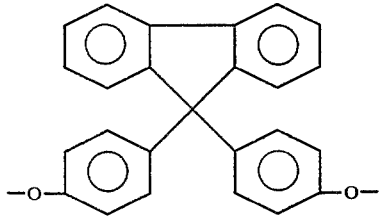

The polyformal was obtained at a 63% yield and formed a tough flexible film by casting or compression molding. It had a $T_g$ of 221° C.

EXAMPLE 9

A mixture of 2.3 parts of (0.01 mole) of bisphenol-A, 1.7 parts (0.026 mole) of 85% pulverized potassium hydroxide, 0.47 parts (0.001 mole) of Aliquat 336 and about 53 parts of methylene chloride were stirred at room temperature under substantially anhydrous conditions for 18 hours. The reaction mixture was then washed with water until it was neutral. Methanol was then added to the mixture resulting in the precipitation of product. There was obtained a 49% yield of polyformal having an intrinsic viscosity of 0.31 dl/g. The polyformal had 42.9% by weight of C-2 through C-17 cyclics based on G.P.C.

EXAMPLE 10

A mixture was stirred in a closed system at 60° C. consisting of 3600 parts of methylene chloride, 119 parts (0.238 mole) of Aliquat 366, 542 parts (2.37 moles) of bisphenol-A and 400 parts (6.2 moles) of potassium hydroxide pellets. The mixture was stirred for about 115 minutes to produce a polyformal having chemically combined bisphenol-A units and formaldehyde units, and 6.7% by weight of cyclics of formula (2).

EXAMPLE 11

A mixture of methylene chloride, N-methylpyrrolidone, potassium hydroxide pellets and 2,2-bis(4-hydroxyphenyl)-butane was stirred at 70° C. under substantially anhydrous conditions for 30 minutes. The mixture had a solids content of about 15% by weight and there was used a proportion of about 52 parts of methylene chloride per 60 parts of N-methylpyrrolidone and a ratio of 2.6 moles of potassium hydroxide per mole of the 2,2-bis(4-hydroxyphenyl)-butane. There was obtained a polyformal consisting essentially of chemically combined formaldehyde units and units of the formula,

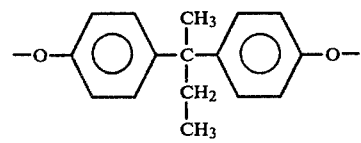

and having an intrinsic viscosity of 1.48 and a $T_g$ of 86° C.

EXAMPLE 12

A mixture of methylene chloride, N-methylpyrrolidone, bisphenol-A, o-hydroxyethylresorcinol and potassium hydroxide pellets was stirred at a temperature of 70° C. for 90 minutes under substantially anhydrous conditions. The mixture had a solids content of 19% by weight and there was utilized a proportion of about 78 parts of methylene chloride per 91 parts of the N-methylpyrrolidone, and a ratio of about 2.6 moles of potassium hydroxide per mole of bisphenol-A per mole of o-hydroxyethylresorcinol. There was obtained a polyformal consisting essentially of chemically combined bisphenol-A units and formaldehyde units and chain terminated with units of the formula,

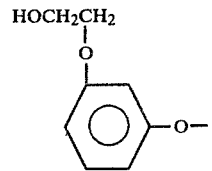

having an intrinsic viscosity of 0.471 dl/g.

EXAMPLE 13

A mixture was stirred under substantially anhydrous conditions consisting of methylene chloride, N-methylpyrrolidone, potassium hydroxide pellets, and 3,3-bis(p-hydroxyphenyl) pentane for a period of about 42 minutes at a temperature of 70° C. The mixture had a solids content of about 18% by weight and a ratio of about 52 parts of methylene chloride per 60 parts of N-methylpyrrolidone and a proportion of about 2.6 moles of potassium hydroxide per mole of the 3,3-bis(p-hydroxyphenyl)-pentane. There was obtained a polyformal having an intrinsic viscosity of 0.831 dl/g, a $T_g$ of 91° C. and consisting essentially of chemically combined formaldehyde units and units of the formula,

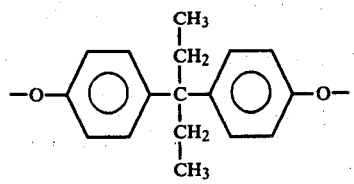

EXAMPLE 14

A mixture of methylene chloride, chlorobenzene, potassium hydroxide pellets, bisphenol-A and Aliquat, the phase transfer catalyst of Example 1, manufactured by the General Mills Company, Chemical Division, was heated and stirred for a period of 7.4 hours at a temperature of 60° C. under a nitrogen atmosphere. The solids content of the mixture was about 20% by weight and there was utilized a mole ratio of 2.6 moles of potassium hydroxide per mole of bisphenol-A. There was also utilized in the mixture a proportion of about 1140 parts of chlorobenzene to 901 parts of methylene chloride. In addition, the Aliquat was employed in the mixture at a proportion of 0.1 mole of Aliquat per mole of bisphenol-A.

Following the procedure of Example 1, there was recovered a 58% yield of a polyformal having an intrinsic viscosity of 0.735 dl/g in chloroform at 25° C. which contained 11% by weight of cyclic polyformal within the scope of formula (2). A clear film was obtained by casting the polymer from a chloroform solution or compression molding it at 150° C. The film is tough and flexible and exhibits a Gardner Impact value of greater than 320 in. lb.

EXAMPLE 15

The procedure of Example 14 was repeated, except that in place of the potassium hydroxide there was utilized 4 moles of sodium hydroxide. In addition, there was utilized a proportion of about 68 parts of chlorobenzene to 20 parts of the methylene chloride. The intercondensation reaction was conducted at a temperature of 75° C. and it was completed within 4 hours. There was obtained a 75% yield of a polyformal consisting essentially of chemically combined formaldehyde units and bisphenol-A units, as shown by Example 1, having an intrinsic viscosity of 0.422 dl/g. A tough flexible film was obtained by casting the polymer from chloroform or compression molding it in accordance with the procedure of Example 1.

EXAMPLE 16

The procedure of Example 7 utilizing methylene bromide was repeated except that in place of Bisphenol-A there was used

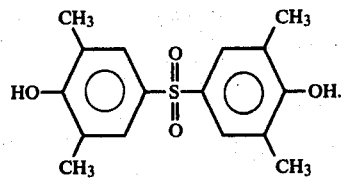

There was obtained a polyformal having a $T_g$ of 175° C. and consisting essentially of chemically combined units of the formula,

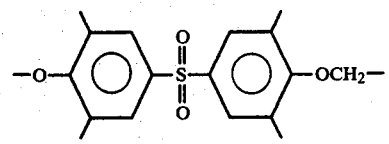

The polyformal was found to be highly insoluble in non-polar organic solvents.

EXAMPLE 17

A mixture of 30 parts (0.1 mole) of 3,4-bis(p-hydroxyphenyl)-3,4-hexanediol, 14.6 parts (0.26 mole) KOH pellets, 81 parts methylene chloride and 93 parts of N-methylpyrrolidone was stirred and heated at reflux (70° C.). After 81 minutes, 11 parts (0.2 mole) more of KOH pellets was added. After 92 minutes the very thick reaction mixture was poured into methanol to recover the polymer. A film forming polyformal was obtained, consisting of formaldehyde units chemically combined with units of the structure,

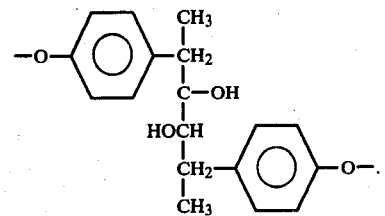

The polymer had an intrinsic viscosity of 0.564 dl/g, and $T_g$ of 67° C.

Although N-methylpyrrolidone was used to make the above polyformal, the present invention provides for the use of a broad variety of dipolar aprotic solvents which can be used in the polyformal reaction mixture at 25° C. to 100° C., and at 5% to 95% by weight, based on the total weight of the mixture.

EXAMPLE 18

There was initially added 9.65 parts of 98.8% by weight of sodium hydroxide pellets to a stirred mixture consisting of 53.5 parts of methylene chloride, 20 parts of 4,4'-thiodiphenol and 16.5 parts of N-methylpyrrolidone. The resulting mixture was stirred and heated to reflux. There was then added three additional increments of sodium hydroxide at the rate of 9.65 parts per 20 minute interval. The intrinsic viscosity of the mixture began to build up in about 71 minutes and the reaction was continued for an additional 40 minutes. The mixture was then allowed to cool and about 150 parts of methanol was added.

There was obtained an 81% yield of product which was washed with water and methanol. Based on method of preparation the product was a polyformal consisting essentially of chemically combined units of the formula,

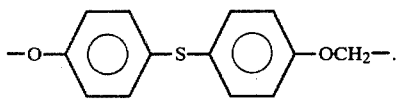

The polyformal was found to be insoluble in chloroform, but could be dissolved in hot tetrachloroethane. It had an intrinsic viscosity of 0.71 dl/g. It was readily converted to a clear film by compression molding having a $T_g$ of 50° C. and $T_m$ of 154° C. A portion of the film formed a crystalline product by allowing it to stand in chloroform at room temperature for 12 hours.

EXAMPLE 19

There was added 13.17 parts of 88.5% by weight of potassium hydroxide pellets to a stirred mixture of 20 parts of 4,4'-sulfonyldiphenol, 100 parts of methylene bromide and 61.5 parts of N-methylpyrrolidone. Three additional portions of potassium hydroxide pellets at 13.17 parts per portion were then added to the stirred mixture at 20 minute intervals while the mixture was refluxing. After the mixture had refluxed for 3 hours, the mixture was allowed to cool and it was poured into methanol. There was obtained a 62% yield of product having an intrinsic viscosity of 0.75 dl/g, a $T_g$ of 177° C. and a $T_m$ of 406° C. Based on method of preparation the product was a polyformal consisting essentially of chemically combined units of the formula,

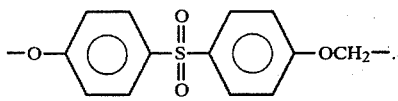

The polyformal was compression molded at 450° F. to produce a clear film. A portion of the film was allowed to stand in chloroform at room temperature for several days. It formed a crystalline product.

EXAMPLE 20

A mixture was stirred and refluxed consisting of 5 parts of bis(4-hydroxyphenyl)methane, 1.23 parts of 89.9% Aliquat 336, 4.12 parts of 88.5% potassium hydroxide and 63 parts of methylene bromide. After refluxing the mixture for 15 minutes it was allowed to cool and then poured into methanol. There was obtained a product which was insoluble in chloroform and soluble in hot N-methylpyrrolidone. The product had a $T_g$ of 54° C. and $T_m$ of 190° C. Based on method of preparation the product was a polyformal consisting essentially of chemically combined units of the formula,

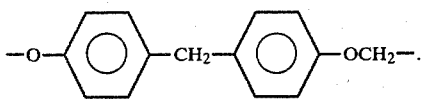

Although the above examples are directed to only a few of the very many variables which can be employed in the practice of the present invention, it should be understood that the present invention is directed to a method for making a much broader class of polyformals consisting essentially of chemically combined units of formula (1) and cyclopolyformals of formula (2) as well as film forming polyformal compositions having less than 10% of chemically combined units of formula (1) in the cyclic state. The cyclic polyformals of formula (2) can be used to make organic solvent resistant wire coating formulations by utilizing such cyclic polyformals in combination with a Lewis acid catalyst and an organic solvent.

What I claim as new and desire to secure by Letters Patent of the United States is:

1. A method for making a polyformal resin having an intrinsic viscosity of greater than 0.3 in chloroform at 25° C. and capable of being compression molded to a flexible film, which comprises
    (1) agitating a mixture containing as essential ingredients, methylene halide, bisphenol, alkali metal hydroxide and a member selected from the class consisting of a phase transfer catalyst and a dipolar aprotic solvent, and
    (2) recovering the polyformal from the mixture of (1), where there is utilized in the reaction mixture per mole of bisphenol, more than 1 mole of methylene halide and greater than 2 moles of alkali metal hydroxide.

2. A method in accordance with claim 1, where a phase transfer catalyst is utilized in the reaction mixture.

3. A method in accordance with claim 1, where a dipolar aprotic solvent is utilized in the reaction mixture.

4. A method in accordance with claim 1, where a substantially inert non-polar organic solvent is utilized in the reaction mixture.

5. A method in accordance with claim 4, where chlorobenzene is utilized in the reaction mixture.

6. A method in accordance with claim 3, where N-methylpyrrolidone is utilized in the reaction mixture.

7. A method in accordance with claim 3, where dimethylsulfoxide is utilized in the reaction mixture.

8. A method in accordance with claim 1, where a temperature in the range of from 25° C. to 100° C. is employed.

9. A method in accordance with claim 1, where the alkali metal hydroxide is potassium hydroxide.

10. A method in accordance with claim 1, where the alkali metal hydroxide is sodium hydroxide.

11. A method for making polyformal resin consisting essentially of chemically combined units of the formula,

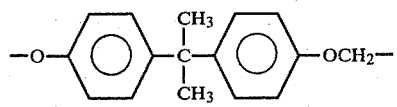

which comprises
    (1) agitating a mixture containing as essential ingredients, methylene chloride, bisphenol-A, potassium hydroxide and a member selected from the class consisting of N-methylpyrrolidone and a phase transfer catalyst at a temperature in the range of from 25° C. to 100° C. and
    (2) recovering polyformal resin from the mixture of (1), where there is utilized per mole of bisphenol-A, more than 1 mole of methylene chloride and more than 2 moles of potassium hydroxide.

12. A method in accordance with claim 11, where monomethyl tricaprylyl ammonium chloride is present in the reaction mixture.

13. A method in accordance with claim 11, where N-methylpyrrolidone is employed in the reaction mixture.

14. A method in accordance with claim 11, where chlorobenzene is employed in the reaction mixture.

15. Cyclopolyformals of the formula,

where R is a divalent aromatic organic radical, and n is an integer equal to from 2 to 25 inclusive.

16. A cyclopolyformal of the formula

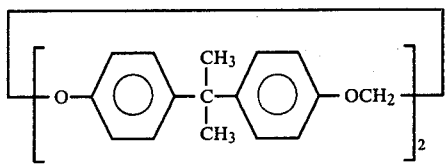

17. A cyclopolyformal of the formula

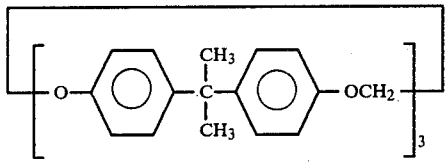

18. A method for making a polyformal consisting essentially of chemically combined units of the formula,

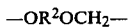

and having less than 10% by weight of such chemically combined units in the cyclic state which comprises
(A) effecting reaction between a bisphenol of the formula,

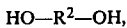

and an alkali metal hydroxide in the presence of a mixture of methylene halide and a dipolar aprotic solvent, and
(B) recovering aromatic polyformal from the mixture of (A), where there is utilized in the reaction mixture of (A) a ratio of 2 to 2.5 moles of alkali metal hydroxide, per mole of bisphenol, while maintaining a concentration of from 20 to 50% by weight of solids, and a weight ratio of 0.8 to 1.2 part of dipolar aprotic solvent, per part of methylene halide, where $R^2$ is selected from the class consisting of $C_{(6-25)}$ divalent aromatic radicals and $R^1Q'R^1$ radicals, where $R^1$ is selected from $C_{(6-13)}$ divalent aromatic radicals and Q' is selected from the class consisting of

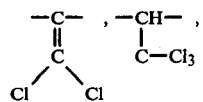

cyclohexyl, fluorenyl, —O—, —S—,

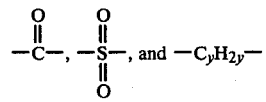

and y is equal to 1 to 5 inclusive.

19. A polyformal consisting essentially of chemically combined units of the formula

—OROCH₂—, having an intrinsic viscosity of at least 0.4 in chloroform at 25° C. and capable of being compression molded to a flexible film and having less than 10% by weight of such chemically combined units in the cyclic state, where R is a $C_{(6-25)}$ divalent aromatic radical selected from phenylene, tolylene, xylylene, naphthalene and —R¹Q-R¹—, where R¹ is a $C_{(6-13)}$ divalent radical and Q can be cyclohexyl, fluorenyl, —O—, —S—,

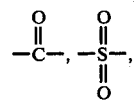

and —$C_yH_{2y}$— and y is equal to 1 to 5 inclusive.

20. A polyformal in accordance with claim 19 where the chemically combined units have the formula,

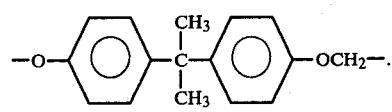

21. A method for making a polyformal resin having an intrinsic viscosity of greater than 0.3 in chloroform at 25° C. and capable of being compression molded to a flexible film which comprises (1) agitating a mixture containing as essential ingredients, methylene halide selected from the group consisting of methylene chloride, methylene bromide and chlorobromomethane, bisphenol, alkali metal hydroxide and a member selected from the class consisting of a phase transfer catalyst and a dipolar aprotic solvent selected from the group consisting of chlorobenzene, dichlorobenzene, benzene, toluene, N-methylpyrrolidone, tetrahydrofuran, dimethylsulfoxide and methylene halide at a temperature of 0° C. to 100° C., and (2) recovering the polyformal from the mixture of (1), where there is utilized in the reaction mixture per mole of bisphenol, more than 1 mole of methylene halide and greater than 2 moles of alkali metal hydroxide.

22. The polyformal resin prepared by the method of claim 21.

* * * * *